(12) United States Patent
Mueller et al.

(10) Patent No.: US 6,774,229 B2
(45) Date of Patent: Aug. 10, 2004

(54) COUPLING CONDENSATION SYNTHESIS OF HETEROCYCLES

(75) Inventors: Thomas Mueller, München (DE); Markus Ansorge, München (DE)

(73) Assignee: Morphochem AG, Munich (DE)

( * ) Notice: Subject to any disclaimer, the term of this patent is extended or adjusted under 35 U.S.C. 154(b) by 0 days.

(21) Appl. No.: 10/151,687

(22) Filed: May 20, 2002

(65) Prior Publication Data

US 2003/0100751 A1 May 29, 2003

Related U.S. Application Data

(63) Continuation of application No. PCT/EP00/11600, filed on Nov. 21, 2000.

(30) Foreign Application Priority Data

Nov. 21, 1999 (DE) .......................................... 199 55 634

(51) Int. Cl.$^7$ .................... C07D 267/02; C07D 281/02; C07D 417/00; C07D 239/00; C07D 239/02
(52) U.S. Cl. .................... 540/544; 546/113; 546/270.7; 548/365.1; 548/379.1; 540/492; 544/242; 544/333
(58) Field of Search .................. 540/492, 544; 546/113, 270.7; 548/365.1, 379.1; 544/242, 333

(56) References Cited

U.S. PATENT DOCUMENTS 6,310,049 B1 * 10/2001 Wada et al. ................... 514/63

OTHER PUBLICATIONS

Müller et al, "An Unexpected Coupling–Isomerization Sequence as an Entry to Novel Three–Component–Pyrazoline Syntheses" Angew. Chem. Int. Ed., vol. 39(7), pp. 1253–1256 (2000).
Müller et al, "A Novel Three–Component One–Pot Pyrimidine Synthesis Based upon a Coupling–Isomerizaton Sequence" Organic Letters, vol. 2(13), pp. 1967–1970 (2000).
Barluenga et al, "One–Pot Synthesis of Qunioxalines and 2,3–Dihydropyrazines via Oxidative Aminomercuration of Propargyl Alcohols" Synthesis. vol. 3, pp. 313–314 (1985).*

* cited by examiner

Primary Examiner—Mukund Shah
Assistant Examiner—Zachary C. Tucker
(74) Attorney, Agent, or Firm—Edwards & Angell, LLP; Jeffrey D. Hsi

(57) ABSTRACT

The invention relates to a process for the preparation of heterocycles, characterised in that the following components:
  i) a propargyl derivative of the general structural formula I

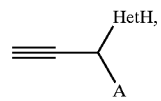

a wherein Het is an optionally substituted hetero atom and A is a substituted or unsubstituted aromatic entity, a substituted or unsubstituted aromatic heterocycle, a substituted or unsubstituted vinyl arene and/or a derivative thereof, an olefin, an alkyne, an acceptor group or a nitrile;
  (ii) a compound of the general structural formula II,

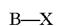

wherein B is an electron-deficient substituted or unsubstituted aromatic entity with or without an acceptor group, an electron-deficient substituted or unsubstituted heteroaromatic entity with or without an acceptor group, an electron-deficient olefin and/or alkyne, a metal complex, and X is a leaving group;
  (iii) a nucleophile of the general structural formula III,

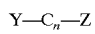

wherein Y and/or Z, each independently of the other, is an amino group, thio group (mercapto group), seleno group, telluro group, hydroxy group (alcohol group), imido group, carbonyl group, thiocarbonyl group, selenocarbonyl group, tellurocarbonyl group; C is a substituted or unsubstituted C atom, a substituted or unsubstituted or annelated CC double bond or single bond and n=0–10, preferably 1–5, preferably are reacted in a one-pot reaction by cyclocondensation to form 4- to 10-membered, preferably 5- to 7-membered, heterocyclic, aromatic or non-aromatic ring systems.

25 Claims, No Drawings

COUPLING CONDENSATION SYNTHESIS OF HETEROCYCLES

This application is a continuation of the PCT/EP/00/11600, filed Nov. 21, 2000.

The invention relates to a process for the preparation of aromatic or non-aromatic heterocycles having from 4 to 10, preferably from 5 to 7, ring members. Those heterocycles are used as fungicides, antimicrobials and bactericides.

In the prior art such ring systems are prepared as follows.

Alkaline condensation (aldol condensation) of an aromatic or heteroaromatic aldehyde with acetyl aromatic entities or acetyl heteroaromatic entities results in the formation of 1,3-diaryl- or -diheteroaryl-substituted enones (chalcones). The substances are isolated and purified. In a second reaction, the chalcones are then reacted with difunctional nucleophiles, for example hydrazines, whereupon the above-mentioned ring systems are obtained.

The process described above has the disadvantage of not being a one-pot process. A one-pot process is understood to mean an especially multi-stage synthesis process wherein any interim products or intermediates are not worked up, for example isolated, concentrated or purified.

Further definitions of terms used hereinbelow are:

An electron-deficient aromatic entity, heteroaromatic entity or olefin/alkyne or, in general, an electron-deficient system is understood to mean a system the π-electron density of which is reduced by negative inductive effects or negative mesomeric effects (-I effects and -M effects, respectively). A list of substituents or groups giving rise to such effects will be found in any standard textbook of organic chemistry. Without limitation, there may be mentioned, as examples of -I substituents: OH, halogens, $NO_2$ and unsaturated groups; and of -M substituents: $NO_2$, CN and aromatic entities. Those electron-withdrawing groups (EWG) must of course be in conjugation with the leaving group X, that is to say in the ortho- or para-position in the case of carbocycles, in order to be capable of exerting the desired effect.

An acceptor group is understood to mean a group that has the following general properties: stabilisation of negative charges and partial charges by means of delocalisation via p-atomic orbitals or π-molecular orbitals (mesomeric stabilisation by means of -M resonance effects, π-acceptor) and/or inductive or field effects of electronegative atoms or molecule moieties (inductive stabilisation by means of -I field effects, σ-acceptor) and combinations of those two effects (for def. see also textbooks of organic chemistry, e.g. Jerry March, Advanced Organic Chemistry, $4^{th}$ edition, Wiley-Interscience, New York, Chichester, Brisbane, Toronto, Singapore, p. 17ff, 36).

Examples of acceptor groups that may be mentioned, without limitation, are: carboxylic, sulphonic, phosphonic and boronic acids, and esters, amides, imides and hydrazides thereof; the cyano group, keto group, formyl group, imine group, trifluoromethyl group, trialkyl-ammonium group, trialkylsilyl group, $\eta^6$-phenylCr(CO)$_3$ and $\eta^6$-6-phenylFe$^+$ cyclopentadienyl complexes.

The problem of the present invention is to make available a one-pot process.

The problem is solved by the process of the invention according to claim 1, wherein the process for the preparation of heterocycles is characterised in that the components:

The invention relates to a process for the preparation of heterocycles, characterised in that the following components:

i) a propargyl derivative of the general structural formula I

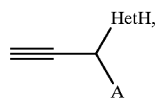

wherein Het is an optionally substituted hetero atom and A is a substituted or unsubstituted aromatic entity, a substituted or unsubstituted aromatic heterocycle, a substituted or unsubstituted vinyl arene and/or a derivative thereof, an olefin, an alkyne, an acceptor group or a nitrile;

(ii) a compound of the general structural formula II

wherein B is an electron-deficient substituted or unsubstituted aromatic entity with or without an acceptor group, an electron-deficient substituted or unsubstituted hetero-aromatic entity with or without an acceptor group, an electron-deficient olefin and/or alkyne, a metal complex, and X is a leaving group;

(iii) a nucleophile of the general structural formula III

wherein Y and/or Z, each independently of the other, is an amino group, thio group (mercapto group), seleno group, telluro group, hydroxy group (alcohol group), imido group, carbonyl group, thiocarbonyl group, selenocarbonyl group, tellurocarbonyl group; C is a substituted or unsubstituted C atom, a substituted or unsubstituted or annelated CC double bond or single bond and n=0–10, preferably 1–5, preferably are reacted in a one-pot reaction by cyclocondensation to form 4- to 10-membered, preferably 5- to 7-membered, heterocyclic, aromatic or non-aromatic ring systems.

Further advantageous embodiments form the subject-matter of the subordinate claims.

The substituents are not subject to any particular limitations. Examples of suitable substituents (preference is given in general to one substituent, but two, three or more substituents are also possible according to the invention) are throughout the description, for example on the aromatic entities, heteroaromatic entities and/or aromatic heterocycles or vinyl arenes, halogen atoms such as chlorine, iodine, fluorine and bromine, aromatic entities such as phenyl groups, alkyl, alkoxy, amino, ester, nitrile, nitro, aldehyde, acetal or sulphone groups. The alkyl and alkoxy groups may be straight-chained or branched. The chain length may be, for example, from 1 to 25, from 1 to 20, from 1 to 15, from 1 to 10 or from 1 to 5 carb as in the case of methyl, ethyl, n-propyl, isopropyl, butyl, tert-butyl; methoxy, ethoxy, n-propoxy, isopropoxy, butoxy, tert-butoxy. The amino groups may be primary, secondary or tertiary. For example, the substituents at the nitrogen atom may be the alkyl groups defined above. In general, all substituents may themselves be substituted, for example by identical substituents.

In the process according to the invention preference is also given to the use of iv) at least one suitable metal catalyst and v) at least one amine compound and/or a metal salt, preferably basic metal salts and mixtures thereof.

In accordance with the invention it is advantageous for the components to be reacted at a temperature of $\geq 0°$ C., preferably $\geq 20°$ C., especially $\geq 70°$ C., in a suitable solvent, suitable solvents including aromatic and heteroaromatic solvents, aliphatic ethers, alcohols, acetonitrile, dimethylformamide, DMSO and water.

In component i), Het may represent, for example, optionally substituted O, S, Se, Te, N, P, As and Sb. Preferably, the electronegativity is equal to or greater than that of carbon (EN≧2.5). As substituents there may be mentioned, for example: for N: tosyl, aminooxy and acyl groups; for P, As and Sb: alkoxy, aryloxy and phosphorimide groups.

The substituent or group A includes those substituents and groups, respectively, that are capable of stabilising negative charges, for example by delocalisation into a π electron system. There are no particular limitations.

The expression "substituted and conjugated and carbocyclically and heterocyclically annelated" compounds means that the compounds may have those features and/or substituents at the same time or individually, with preference being given to unsubstituted compounds.

There follow specific, non-limiting examples of substituents A of component i), wherein alkyl groups may be defined as mentioned hereinbefore:

Aromatic entities selected from the group of substituted and unsubstituted and conjugated and carbocyclically and heterocyclically annelated alkyl- and aryl-benzenes, phenols, aryl ketones, aryl thioketones, benzaldehydes, anilines, alkyl- and aryl-aryl ethers, benzodioxoles, arylalkyl and arylaryl thioethers, arylalkyl selenoethers, arylaryl selenoethers, arylalkyl telluroethers, arylaryl telluroethers, sulphoxybenzenes, sulphonyl benzenes, dialkylaryl- and triaryl-phosphanes, dialkylaryl- and triaryl-phosphane oxides, dialkylaryl- and triaryl-arsanes, dialkylaryl- and triaryl-arsane oxides, dialkylaryl- and triaryl-stibanes, dialkylaryl- and triaryl-stibane oxides, benzonitriles, benzoic acid esters, benzoic acid thioesters, benzoic acid selenoesters, benzoic acid telluroesters, benzamides, benzothioamides, benzourethanes and benzoureas; including derivatives and mixtures thereof. Aryl radicals preferably have 6, 10 or 14 ring C atoms. Special preference is given to phenols.

Aromatic heterocycles or heteroaromatic entities, selected from the group of substituted and unsubstituted and conjugated and carbocyclically and heterocyclically annelated thiophenes, selenophenes, tellurophenes, furans, pyrroles, indoles, quinolines, isoquinolines, pyridines, pyrimidines, pyrazines, bipyridines, bipyrimidines, bipyrazines, triazines, tetrazines, oxazoles, isooxazoles, thiazoles, imidazoles, triazoles, azepines, oxazepines, dioxins, phenoxazines, phenothiazines, porphyrins, corrins and phthalocyanines; including derivatives and mixtures thereof.

Vinyl arenes selected from the group of substituted and unsubstituted and conjugated and carbocyclically and heterocyclically annelated styrenes, indenes, indoles, benzofurans, benzothiophenes and benzoselenophenes; including derivatives and mixtures thereof.

Electron-deficient olefins selected from the group of substituted and unsubstituted and conjugated and carbocyclically and heterocyclically annelated acrylic alkyl and aryl esters, acrylic alkyl and aryl thioesters, vinyl ketones, vinyl thioketones, acroleins, vinyl sulphones, vinyl sulphoxides, vinyl phosphane oxides, vinyl phosphonic acid dialkyl and diaryl esters, acrylonitriles, acrylamides and acrylothioamides; including derivatives and mixtures thereof. The compounds preferably have from 2 to 20, especially from 2 to 10 or from 2 to 6 C, atoms.

Acceptor groups selected from the group of substituted and unsubstituted and conjugated and carbocyclically and heterocyclically annelated trialkylsilyl groups, keto groups, which contain for example from 1 to 6 C atoms, formyl groups, carboxylic, sulphonic, phosphonic and boronic acids and benzotriazole groups; including derivatives and mixtures thereof.

There follow specific, non-limiting examples of substituents B of component ii):

Electron-deficient aromatic entities selected from the group of substituted and unsubstituted and conjugated and carbocyclically and heterocyclically annelated nitrobenzenes, benzaldehydes, benzonitriles, benzoic acid esters, alkylaryl and arylaryl ketones, alkylaryl and arylaryl sulphones, alkylaryl and arylaryl sulphoxides, dialkylaryl- and triaryl-phosphane oxides, dialkylaryl- and triaryl-arsane oxides and dialkylaryl- and triaryl-stibane oxides; including derivatives and mixtures thereof. The aldehyde, ester, keto and/or alkyl groups of those electron-deficient aromatic entities preferably have from 1 to 6 C atoms.

Electron-deficient heteroaromatic entities selected from the group of substituted and unsubstituted and conjugated and carbocyclically and heterocyclically annelated quinolines, isoquinolines, pyridines, pyrimidines, pyrazines, bipyridines, bipyrimidines, bipyrazines, triazines, tetrazines, oxazoles, isooxazoles, thiazoles, imidazoles and triazoles; including derivatives and mixtures thereof.

Electron-rich heteroaromatic entities having at least one acceptor group, selected from the group of substituted and unsubstituted and conjugated and carbocyclically and hetero-cyclically annelated thiophenes, selenophenes, tellurophenes, furans, pyrroles, indoles, quinolines, isoquinolines, azepines, oxazepines, dioxins, phenoxazines, phenothiazines, porphyrins, corrins and phthalocyanines; including derivatives and mixtures thereof.

Electron-deficient olefins selected from the group of substituted and unsubstituted and conjugated and carbocyclically and heterocyclically annelated acrylic alkyl and aryl esters, acrylic alkyl and aryl thioesters, vinyl ketones, vinyl thioketones, acroleins, vinyl sulphones, vinyl sulphoxides, vinyl phosphane oxides, vinyl phosphonic acid dialkyl and diaryl esters, acrylonitriles, acrylamides and acrylothioamides; including derivatives and mixtures thereof. The aldehyde, ester, keto and/or alkyl groups of those electron-deficient olefins preferably have from 1 to 6 C atoms.

Metal complexes selected from the group of substituted and unsubstituted and conjugated and carbocyclically and heterocyclically annelated tricarbonylchromium-complexed arenes and heteroarenes, tricarbonylmanganese-complexed arene salts, cyclopentadienyl-iron- and -ruthenium-complexed arene salts, tricarbonyliron-complexed butadienes and hexacarbonyldicobalt-complexed alkynes; including derivatives and mixtures thereof.

There follow specific, non-limiting examples of the leaving group X. Halogens, for example I, Cl, Br and F, substituted and unsubstituted phosphates, sulphates, triflates, nonaflates, sulphonates, sulphinates and/or alkyl and aryl esters thereof; including derivatives and mixtures thereof.

There follow specific, non-limiting examples of component iii):

Of advantage are bis-functional or higher functional nucleophiles, for example hydrazines, hydroxylamines, ureas, thioureas, amidines and salts thereof, and also those selected from the group of substituted and unsubstituted and conjugated and carbocyclically and heterocyclically annelated phenylenediamines, aminophenols, aminothiophenols, diaminoalkanes, diaminoaryl and diaminoheteroaryl compounds, aminohydroxyaryl and aminohydroxyheteroaryl compounds, aminomercaptoaryl and aminomercaptoheteroaryl compounds, aminoselenoaryl and aminoselenoheteroaryl compounds, β-aminovinyl esters, β-aminovinyl ketones, β-aminovinyl aldehydes, β-aminovinyl imines, β-aminovinyl sulphones and β-aminovinyl trifluoromethanes; including derivatives and mixtures thereof. The aldehyde, ester, keto and/or alkyl groups of those compounds preferably have from 1 to 6 C atoms.

There follow specific, non-limiting examples of component iv):

Suitable as metal catalyst are, for example, bis(triarylphosphane)palladium(II) halides, bis(triheteroarylphosphane)palladium(II) halides, tetrakis(triarylphosphane)palladium(0), tetrakis(triheteroarylphosphane)palladium(0), bis(dibenzylidenacetone)palladium(0) and triarylphosphanes, palladium(II) halides and triarylphosphanes, palladium(II) halides and triheteroarylphosphanes, bis(benzonitrile)palladium(II) halides and triarylphosphanes, bis(benzonitrile)palladium(II) halides and triheteroarylphosphanes, bis(acetonitrile)-palladium(II) halides and triarylphosphanes, and bis(acetonitrile) palladium(II) halides and triheteroarylphosphanes; and also the analogous nickel and platinum complexes; including derivatives and mixtures thereof.

There follow specific, non-limiting examples of component v):

Suitable as amine compound are, for example, aliphatic and/or aromatic primary, secondary and tertiary amines; including derivatives and mixtures thereof. The secondary and tertiary amines preferably have alkyl groups containing from 1 to 6 carbon atoms.

Suitable as metal salt are, for example, acetates, carbonates and hydroxides of ammonium, of alkali metals, of alkaline earth metals, of aluminium, of gallium, of indium, of thallium and of silver; including derivatives and mixtures thereof.

Of special advantage are, for example, halides, acetates, triflates, sulphates and carbonates of copper(I) and of copper(II); including derivatives and mixtures thereof.

In accordance with the invention, for example, to obtain the compound 5-[4'-methyl-2'-(2"-pyridylamino)thiazol-5'-yl]-2-(4'-pyridyl)pyrazoline, there may be cyclocondensed component i) of structural formula

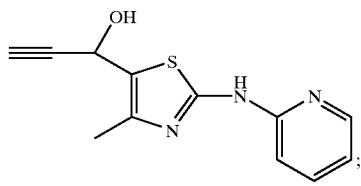

component ii) of structural formula

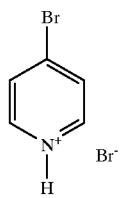

and component iii) of structural formula

H₂N—NH₂.

Using the process according to the invention it is advantageously possible to prepare aromatic or non-aromatic heterocycles having from 4 to 10, preferably from 5 to 7, ring members, having fungicidal, antimicrobial and/or bactericidal properties, including the following compounds IV to VII.

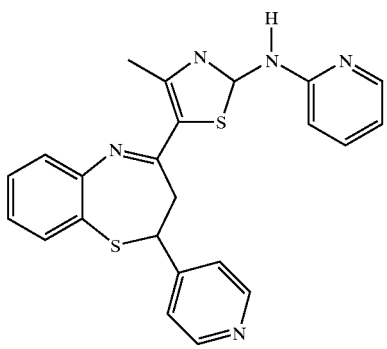

IV

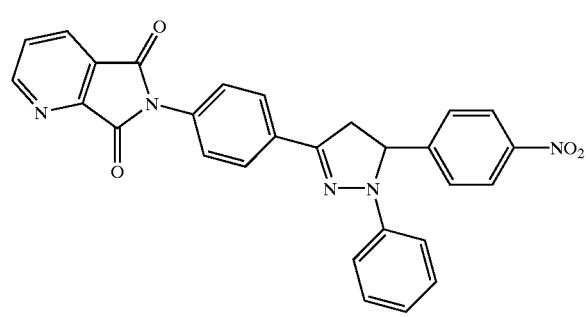

V

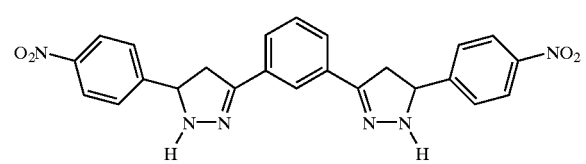

VI

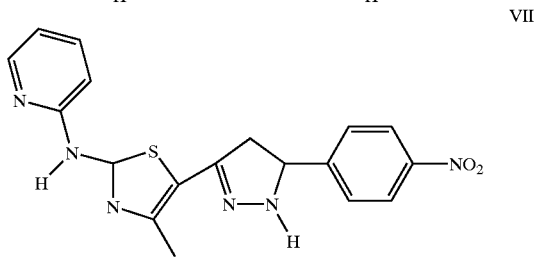

VII

The invention relates also to the use of heterocycles prepared in accordance with the process of the invention as fungicides, antimicrobials and/or bactericides. It will be clear that these heterocycles may be equally suitable for all or only one or more of those intended uses. Suitability for the purpose in question may be determined by means of simple routine tests.

The invention accordingly relates also to a fungicidal, antimicrobial and/or bactericidal composition that consists of, or comprises, one or more heterocycles prepared in accordance with the process of the invention, optionally in combination with an extender, adjuvant or carrier suitable for fungicides, antimicrobials and/or bactericides. It will be clear that such a composition must comprise an effective dose of the heterocycle in question, which may be determined by means of simple routine tests.

The invention is illustrated hereinbelow, without limitation, with reference to specific embodiments and examples.

The interest in consecutive reactions is ever increasing because, by means of efficient syntheses, a maximum of structural complexity can be built up in a few steps, with high chemo-, regio- and stereo-selectivity, from simple starting materials and in good yields. In each case, in the immediately preceding reaction there is formed the functionality necessary for the subsequent step. For the development of new cascade reactions, especially with respect to multi-component reactions, the in situ production of reactive functional groups is therefore a particular challenge. Ideally, then, all those processes proceed, where appropriate with successive addition of reagents, without isolation of intermediates, as in the case of "one-pot synthesis". Good examples of such consecutive processes are both multi-component condensations and also palladium-catalysed cascade reactions, which in many cases have been found to be especially versatile not least because of the mild reaction conditions and the marked toleration by functional groups.

In the course of work by the inventors in regard of the chemistry of areneCr(CO)$_3$ complexes having conjugated side chains it has now been found that the otherwise very reliable Sonogashira coupling of chloroarene complexes 1 with 1-arylprop-2-ynolene 2 does not result in the expected alkyne coupling products (the propargyl alcohols 3), but rather that the isomeric aryl-complexed chalcones 4 are formed in good yields (Scheme 1).

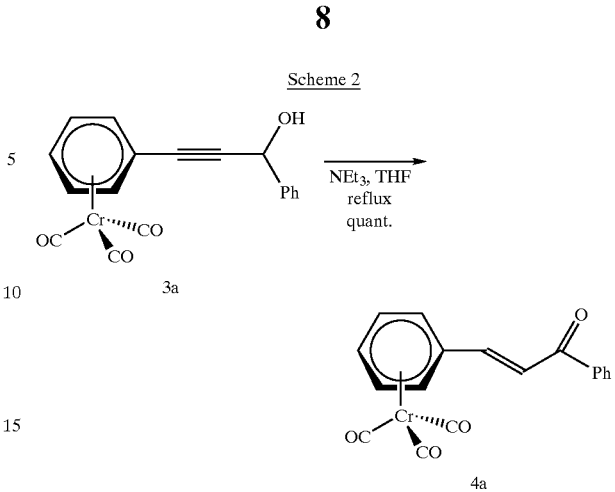

With the aid of a selectively $^1$H-decoupled $^{13}$C-NMR experiment, it has been possible to elucidate, without any doubt, the structure of the complexed chalcone 4a and consequently rule out the possibility of a Meyer-Schuster rearrangement. Notably, the chalcones are formed with excellent trans-selectivity ($J^3$=16 Hz), which indicates, inter alia, thermodynamically controlled formation of the double bond.

It has been found that the isomerisation proceeds in exclusively base-catalysed manner, because when the complexed diphenylpropargyl alcohol 3a ($R^1$=H, $R^2$=Ph) (the presumed intermediate of the Sonogashira coupling of 1a with 2a) is heated in THF in the presence of triethylamine, the complexed chalcone 4a is rapidly formed (Scheme 2).

On the other hand, if coupling of the propargyl alcohol 2a is carried out with, instead of the chlorobenzene complex, iodobenzene (5), which relatively rapidly enters into oxidative addition at the palladium complex, the diphenylpropargyl alcohol (6) is formed exclusively (Scheme 3). The electronic nature of the haloarene component obviously plays a key role in the subsequent isomerisation. It is therefore assumed that this coupling-isomerisation sequence is far more generally applicable than only to heteroaromatic entities and chromiumcarbonyl-complexed arenes.

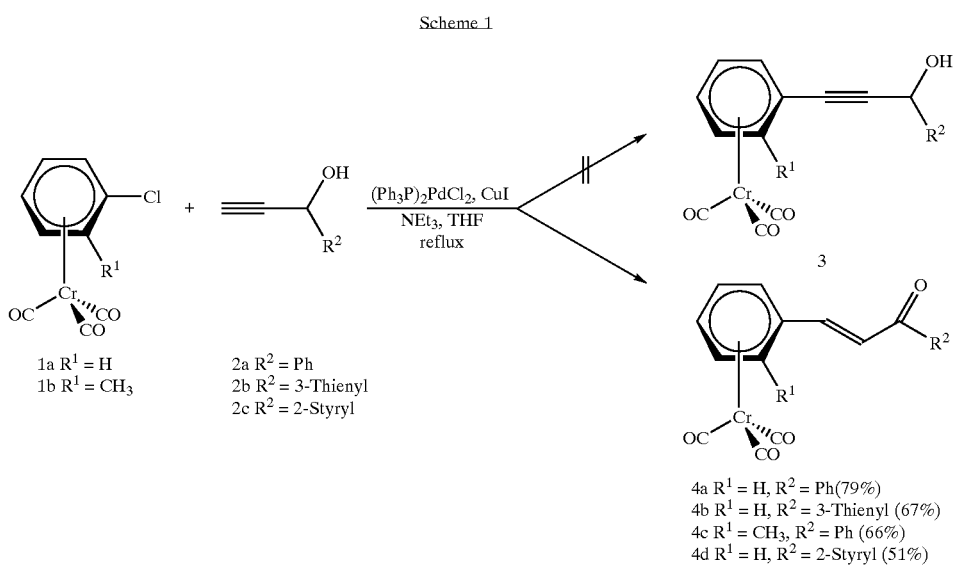

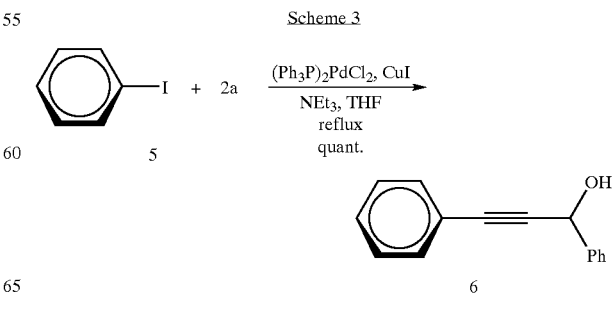

If the halogen component 7 has an electron-withdrawing group (EWG, for example one having an -I or -M effect) in conjugation (that is to say, in the case of carbocycles, an EWG in the ortho- or para-position) with respect to the halogenated carbon atom, as, for example, in the case of acceptor-substituted halo(hetero)arenes, Z-3-bromoacrylic acid ester or 3-bromocyclohex-2-enone, and if the substituent at the propargyl centre in 2 is an extended π system, then the enones 8 are formed in good to very good yields (Scheme 4, Table 1).

Scheme 4

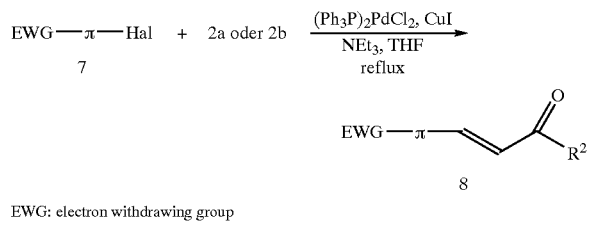

EWG: electron withdrawing group

On the basis of the product analysis and control experiment with respect to the base-catalysed isomerisation of 3a to 4a, the mechanistic course of this coupling-isomerisation sequence can accordingly be schematically represented as follows (Scheme 5).

The Sonogashira coupling of the terminal arylpropargyl alcohol 2 with a sufficiently electron-deficient sp²-hybridised halogenated coupling partner 7 results in the formation of an acceptor-substituted propargyl alcohol 9.

Under equilibrium conditions, the base triethylamine deprotonates at the propargyl centre, whereupon a resonance-stabilised propargyl-allenyl anion 10 is formed, which is protonated to form the thermodynamically more advantageous allene 11. The concluding allenol-enone tautomerism results selectively in the formation of the trans-configured enone 8.

The mild reaction conditions show that this coupling-isomerisation sequence is a competitive means of enone synthesis compared to aldol condensation, especially when the corresponding aldehyde component is not readily accessible (for example, the corresponding 3-formyl-cyclohex-2-enone) or when an alkali-sensitive functionality (7b, 7c, 7d) has to be taken through the reaction without an onerous protecting group strategy. In addition, propargyl alcohols are substantially easier to handle than vinyl ketones, which can be coupled in the course of a Heck reaction to form enones but have a pronounced tendency to polymerisation. Interestingly, the coupling-isomerisation reaction results in complete Z-E-isomerisation of the double bond of the acrylic ester fragment (8e), which, inter alia, also assists thermodynamically controlled formation of the enone functionality (via delocalisation of the intermediately generated negative charge at the propargyl centre). Sonogashira couplings, on the other hand, proceed stereospecifically, with the alkene configuration being obtained. By this means it is possible, simply and stereoselectively, for electron-deficient dienes (8e, 8f) to be synthesised, which in turn constitute interesting substrates for Diels-Alder reactions having an inverse electron requirement.

TABLE 1

Coupling-isomerisation reaction.

| No. | EWG-π-Hal 7 | Propargyl alcohol 2 | Enone 8[a] | Yield [%][b] |
|---|---|---|---|---|
| 1 | 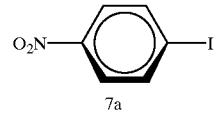 7a | 2a R² = Ph | 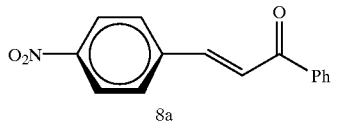 8a | 80 |
| 2 | 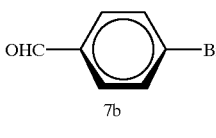 7b | 2a R² = Ph | 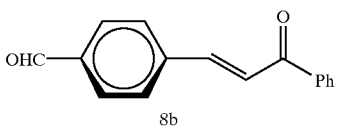 8b | 57 |
| 3 | 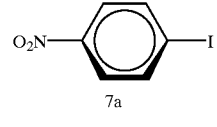 7a | 2b R² = 3-Thienyl | 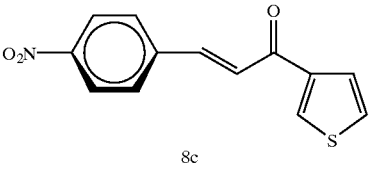 8c | 100 |
| 4 | 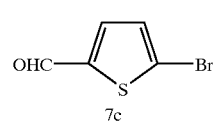 7c | 2a R² = Ph | 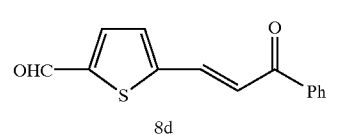 8d | 85 |

TABLE 1-continued

Coupling-isomerisation reaction.

| No. | EWG-π-Hal 7 | Propargyl alcohol 2 | Enone 8[a] | Yield [%][b] |
|---|---|---|---|---|
| 5 | 7d (H₃CO₂C-CH=CH-Br) | 2b R² = 3-Thienyl | 8e | 90 |
| 6 | 7e (3-bromocyclohex-2-enone) | 2b R² = 3-Thienyl | 8f | 97 |

[a]The compounds 8 were unambiguously characterized by $^1$H- and $^{13}$C-NMR, IR and mass spectrometry and by elemental analysis and high-resolution mass spectrometry. [b]The yields are based on products that have been isolated and chromatographically purified.

Furthermore, this mild enone synthesis makes it possible to develop new one-pot reactions, which can proceed using the newly formed enone functionality. Under the reaction conditions, it is possible, inter alia, to add N-methylhydrazine after coupling has been carried out, because only after the base-catalysed isomerisation of the propargyl alcohols to form the enones does the hydrazine react, by Michael addition in the course of cyclising condensation, with the α,β-unsaturated carbonyl compounds to form 2-pyrazolines 12 (Scheme 6, Table 2), without its being necessary for the enone to be isolated beforehand.

Scheme 5

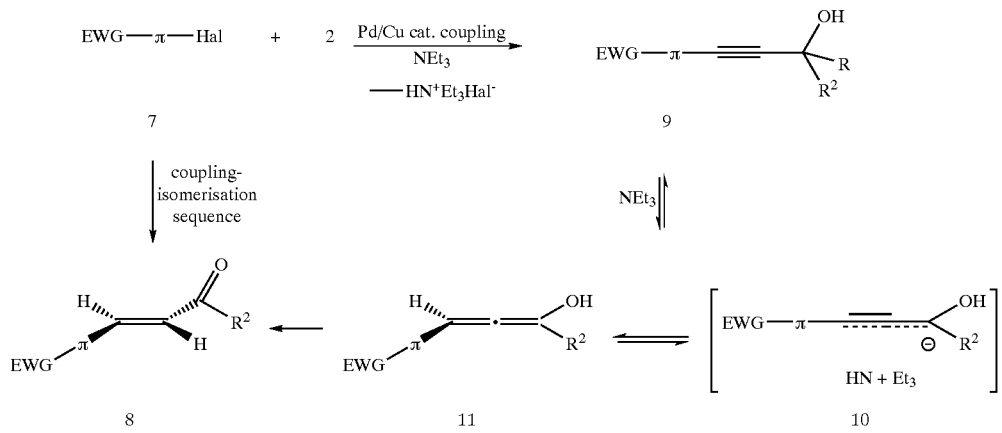

EWG: electron withdrawing group

Scheme 6

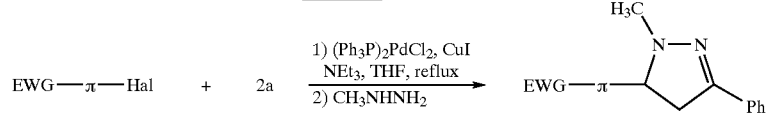

EWG: electron withdrawing group

The one-pot synthesis according to the invention of 3,5-disubstituted 2-pyrazolines, an important class of pharmaceutical precursors, allows new retro-synthesis steps for the construction of heterocyclic systems, using a coupling-isomerisation sequence, from an aryl halide, a propargyl alcohol and a hydrazine (Scheme 7). Further heterocycle syntheses, including those having a combinatorial objective, are now readily conceivable on the basis of this coupling-isomerisation sequence.

Scheme 7

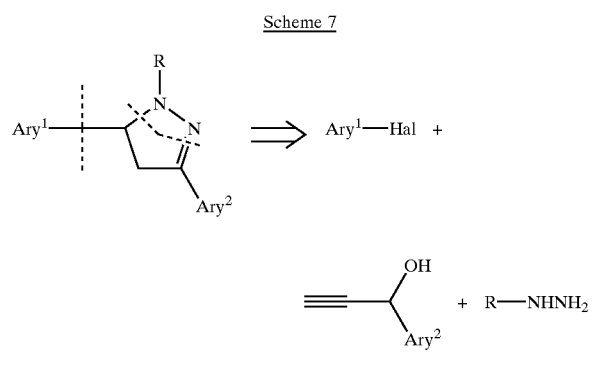

EXAMPLES

Enone synthesis (8a): To a solution of 0.25 g (1.00 mmol) of 7a, 22 mg (0.02 mmol) of Pd(PPh$_3$)$_2$Cl$_2$ and 2 mg (0.01 mmol) of CuI in 10 ml of anhydrous THF and 5 ml of triethylamine under nitrogen there is added, dropwise, over the course of 30 min, a solution of 0.14 g (1.05 mmol) of 2a in 10 ml of THF and the reaction mixture is then boiled under reflux for 10 hours. After cooling, 30 ml of diethyl ether are added to the mixture, and the mixture is filtered. The crude product obtained after removal of the solvents in vacuo is adsorptively filtered over silica gel (10 cm, diameter 1 cm; eluant: diethyl ether/pentane). 0.40 g (80%) of 8a, melting pt. 161–162° C., is obtained.

One-pot pyrazoline synthesis (12a): To a solution of 0.25 g (1.00 mmol) of 7a, 22 mg (0.02 mmol) of Pd(PPh$_3$)$_2$Cl$_2$ and 2 mg (0.01 mmol) of CuI in 10 ml of anhydrous THF and 5 ml of triethylamine under nitrogen there is added, dropwise, over the course of 30 min, a solution of 0.14 g (1.05 mmol) of 2a in 10 ml of THF and the reaction mixture is then boiled under reflux for 10 hours. After cooling, 0.15 ml (3.76 mmol) of N-methylhydrazine is added and boiling under reflux is carried out for a further 5 hours. The crude product obtained after removal of the solvents in vacuo is adsorptively filtered over silica gel (10 cm, diameter 1 cm; eluant: diethyl ether/pentane). 0.26 g (92%) of 12a, melting pt. 118–119° C., is obtained.

TABLE 2

Three-component pyrazoline synthesis

| No. | EWG-π-Hal | Pyrazoline 12[a] | Yield [%][b] |
|---|---|---|---|
| 1 | 7a | 12a | 90 |
| 2 | 1a | 12b | 63 |
| 3 | 7f | 12c | 77 |
| 4 | 7g | 12d | 69 |

[a]The compounds 12 were unambiguously characterized by NMR, IR and mass spectrometry and by elemental analysis and high-resolution mass spectrometry. [b]The yields are based on products that have been isolated and chromatographically purified.

What is claim is:

1. Process for the preparation of heterocycles comprising reacting the following components:

(i) a propargyl derivative of the general structural formula I

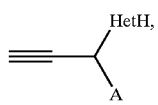

I wherein Het is an optionally substituted hetero atom and A is a substituted or unsubstituted aromatic entity, a substituted or unsubstituted aromatic heterocycle, a substituted or unsubstituted vinyl arene, an olefin, an alkyne, a nitrile, or an acceptor group chosen from among carboxylic acid, ester, amide, imide or hydrazide; sulphonic acid, ester, amide, imide or hydrazide; phosphonic acid, ester, amide, imide or hydrazide; boronic acid, ester, amide, imide or hydrazide; cyano; heto; formyl; imine; trifluoromethyl; trialkylammonium; trialkylsilyl; $\eta^6$-phenyl(Cr(CO)$_3$; and $\eta^6$-6-phenylFe+cyclopentadienyl complex;

(ii) a compound of the general structural formula II

II, wherein B is an electron-deficient substituted or unsubstituted aromatic entity, an electron-deficient substituted or unsubstituted heteroaromatic entity with or without an acceptor group, an electron-deficient olefin and/or alkyne, and X is a leaving group;

(iii) a nucleophile of the general structural formula III

III, wherein Y and/or Z, each independently of the other, is an amino group, thio group (mercapto group), seleno group, telluro group, hydroxy group (alcohol group); C is a substituted or unsubstituted C atom or atoms, where double or single bonds may be represent between said C atoms, and n=0–10 in a one-pot reaction by cyclocondensation to form one or more 5- to 10-membered heterocyclic, aromatic or non-aromatic ring systems.

2. Process according to claim 1, wherein further iv) at least one suitable metal catalyst; and v) at least one amine compound and/or a metal salt is used.

3. Process according to claim 1 or 2, wherein the components are reacted at a temperature of $\geq 0°$ C. in a suitable solvent.

4. Process according to claim 1, wherein substituent A of component i) is an aromatic entity selected from the group consisting of substituted and unsubstituted and conjugated and carbocyclically and heterocyclically annelated alkyl- and aryl-benzenes, phenols, aryl ketones, aryl thioketones, benzaldehydes, anilines, alkyl- and aryl-aryl ethers, benzodioxoles, arylalkyl and arylaryl thioethers, arylalkyl selenoethers, arylaryl selenoethers, arylalkyl telluroethers, arylaryl telluroethers, sulphoxybenzenes, sulphonyl benzenes, dialkylaryl- and triaryl-phosphanes, dialkylaryl- and triaryl-phosphane oxides, dialkylaryl- and triaryl-arsanes, dialkylaryl- and triaryl-arsane oxides, dialkylaryl- and triaryl-stibanes, dialkylaryl- and triaryl-stibane oxides, benzonitriles, benzoic acid esters, benzoic acid thioesters, benzoic acid selenoesters, benzoic acid telluroesters, benzamides, benzothioamides, benzourethanes and benzoureas.

5. Process according to claim 1, wherein substituent A of component i) is an aromatic heterocycle selected from the group consisting of substituted and unsubstituted and conjugated and carbocyclically and heterocyclically annelated thiophenes, selenophenes, tellurophenes, furans, pyrroles, indoles, quinolines, isoquinolines, pyridines, pyrimidines, pyrazines, bipyridines, bipyrimidines, bipyrazines, triazines, tetrazines, oxazoles, isooxazoles, thiazoles, imidazoles, triazoles, azepines, oxazepines, dioxins, phenoxazines, phenothiazines, porphyrins, corrins and phthalocyanines.

6. Process according to claim 1, wherein substituent A of component i) is a vinyl arene selected from the group of substituted and unsubstituted and conjugated and carbocyclically and heterocyclically annelated styrenes, indenes, indoles, benzofurans, benzothiophenes and benzoselenophenes.

7. Process according to claim 1, wherein substituent A of component i) is an electron-deficient olefin selected from the group consisting of substituted and unsubstituted and conjugated and carbocyclically and heterocyclically annelated acrylic alkyl and aryl esters, acrylic alkyl and aryl thioesters, vinyl ketones, vinyl thioketones, acroleins, vinyl sulphones, vinyl sulphoxides, vinyl phosphane oxides, vinyl phosphonic acid dialkyl and diaryl esters, acrylonitriles, acrylamides and acrylothioamides.

8. Process according to claim 1, wherein the substituent B of component ii) is an electron-deficient aromatic entity selected from the group consisting of substituted and unsubstituted and conjugated and carbocyclically and heterocyclically annelated nitrobenzenes, benzaldehydes, benzonitriles, benzoic acid esters, alkylaryl and arylaryl ketones, alkylaryl and arylaryl sulphones, alkylaryl and arylaryl sulphoxides, dialkylaryl and triaryl phosphane oxides, dialkylaryl and triaryl arsane oxides, and dialkylaryl and triaryl stibane oxide.

9. Process according to claim 1, wherein substituent B of component ii) is an electron-deficient heteroaromatic entity selected from the group consisting of substituted and unsubstituted and conjugated and carbocyclically and heterocyclically annelated quinolines, isoquinolines, pyridines, pyrimidines, pyrazines, bipyridines, bipyrimidines, bipyrazines, triazines, tetrazines, oxazoles, isooxazoles, thiazoles, imidazoles and triazoles.

10. Process according to claim 1, wherein substituent B of component ii) is an electron-deficient heteroaromatic having at least one acceptor group, selected from the group consisting of substituted and unsubstituted and conjugated and carbocyclically and heterocyclically annelated thiophenes, selenophenes, tellurophenes, furans, pyrroles, indoles, quinolines, isoquinolines, azepines, oxazepines, dioxins, phenoxazines, phenothiazines, porphyrins, corrins and phthalocyanines.

11. Process according to claim 1, wherein substituent B of component ii) is an electron-deficient olefin selected from the group consisting of substituted and unsubstituted and conjugated and carbocyclically and heterocyclically annelated acrylic alkyl and aryl esters, acrylic alkyl and aryl thioesters, vinyl ketones, vinyl thioketones, acroleins, vinyl sulphones, vinyl sulphoxides, vinyl phosphane oxides, vinyl phosphonic acid dialkyl and diaryl esters, acrylonitriles, acrylamides and acrylothioamides.

12. Process according to claim 1, wherein X is a leaving group selected from the group consisting of halogens, substituted and unsubstituted phosphates, sulphates, triflates, nonaflates, sulphonates, sulphinates and/or alkyl and aryl esters thereof.

13. Process according to claim 2, wherein the metal catalyst iv) is selected from the group consisting of bis(triarylphosphane)palladium(II) halides, bis(triheteroarylphosphane)palladium(II) halides, tetrakis(triarylphosphane)palladium(0), tetrakis(triheteroarylphosphane)palladium(0), bis(dibenzylidenacetone)palladium(0) and triarylphosphanes, palladium(II) halides and triarylphosphanes, palladium(II) halides and triheteroarylphosphanes, bis(benzonitrile)palladium(II) halides and triarylphosphanes, bis(benzonitrile)palladium(II) halides and triheteroarylphosphanes, bis(acetonitrile)palladium(II) halides and triarylphosphanes, and bis(acetonitrile)palladium(II) halides and triheteroarylphosphanes; and nickel and platinum complexes; including mixtures thereof.

14. Process according to claim 2, wherein the amine compound v) is selected from the group consisting of aliphatic and/or aromatic primary, secondary and tertiary amines; including mixtures thereof.

15. Process according to claim 2, wherein the metal salt v) is selected from the group consisting of acetates, carbonates and hydroxides of ammonium, of alkali metals, of alkaline earth metals, of aluminum, of gallium, of indium, of thallium and of silver; including mixtures thereof.

16. Process according to claim 2, wherein the metal salt v) is selected from the group consisting of halides, acetates, triflates, sulphates and carbonates of copper(I) and of copper (II); including mixtures thereof.

17. Process according to claim 1, wherein, to obtain the compound 5-[4'-methyl-2'-(2"-pyridylamino)thiazol-5'-yl]-2-(4'-pyridyl)pyrazoline, there are cyclocondensed component i) of structural formula

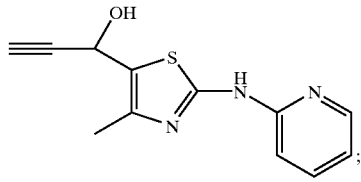

component ii) of structural formula

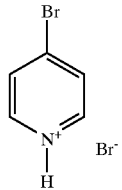

and component iii) of structural formula

18. The process of claim 1 wherein n is 1–5.

19. The process of claim 1 wherein the cyclocondensation forms a 5- to 7-membered heterocyclic, aromatic or non-aromatic ring system.

20. The process of claim 3 wherein the components are reacted at a temperature of $\geq 70°$ C.

21. The process of claim 3 wherein the components are reacted in a solvent of an aromatic solvent, a heteroaromatic solvent, an aliphatic ether, an alcohol, acetonitrile, dimethylformamide, or DMSO and water.

22. Process for the preparation of heterocycles comprising reacting the following components:

(i) a propargyl derivative of the general structural formula I

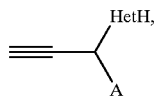

wherein Het is an optionally substituted hetero atom and A is a substituted or unsubstituted aromatic entity, a substituted or unsubstituted aromatic heterocycle, a substituted or unsubstituted vinyl arene, an olefin, an alkyne, nitrile, or an acceptor group chosen from among carboxylic acid, ester, amide, imide or hydrazide; sulphonic acid, ester, amide, imide or hydrazide; phosphonic acid, ester, amide, imide or hydrazide; boronic acid, ester, amide,imide or hydrzide; cyano; keto;formyl; imide; trifluoromethyl; trialkylammonium; trialkylsilyl; $\eta^6$-phenyl(Cr(CO)$_3$; and $\eta_6$-6-phenylFe+cyclopentadienyl complex, (ii) a compound of the general structural formula II wherein B is an electron-deficient substituted or unsubstituted aromatic entity with or without an acceptor group, an electron-deficient substituted or unsubstituted heteroaromatic entity, an electron-deficient olefin and/or alkyne, and X is a leaving group;

(iii) a nucleophile selected from the group consisting of hydrazines, hydroxylamines, ureas, thioureas, amidines and salts thereof, and also selected from the group of substituted and unsubstituted and conjugated and carbocyclically and heterocyclically annelated phenylenediamines, aminophenols, aminothiophenols, diaminoalkanes, diaminoaryl and diaminoheteroaryl compounds, aminohydroxyaryl and aminohydroxyheteroaryl compounds, aminomercaptoaryl and aminomercaptoheteroaryl compounds, aminoselenoaryl and aminoselenoheteroaryl compounds, β-aminovinyl esters, β-aminovinyl ketones, β-aminovinyl aldehydes, β-aminovinyl imines, β-aminovinyl sulphones and β aminovinyl trifluoromethanes in a one-pot reaction by cyclocondensation to form one or more 5- to 10-membered heterocyclic, aromatic or non-aromatic ring systems.

23. The process of claim 22 further comprising use of iv) at least one suitable metal catalyst; and v) at least one amine compound and/or a metal salt.

24. The process of claim 22 or 23 wherein the components are reacted at $\geq 0°$ C.

25. The process of claim 22 or 23 wherein the components are reacted at $\geq 70°$ C.

* * * * *